(12) United States Patent  (10) Patent No.: US 9,737,347 B2
Schlienger et al.  (45) Date of Patent: Aug. 22, 2017

(54) SURGICAL NAIL

(75) Inventors: André Schlienger, Arlesheim (CH);
Markus Buettler, Mümliswil (CH);
Peter Senn, Waldenburg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2760 days.

(21) Appl. No.: 11/299,337

(22) Filed: Dec. 9, 2005

(65) Prior Publication Data
US 2006/0149248 A1 Jul. 6, 2006

Related U.S. Application Data

(63) Continuation of application No. PCT/CH03/00376, filed on Jun. 12, 2003.

(51) Int. Cl.
A61B 17/72 (2006.01)
A61B 17/00 (2006.01)

(52) U.S. Cl.
CPC .......... A61B 17/72 (2013.01); A61B 17/7241 (2013.01); A61B 2017/00004 (2013.01)

(58) Field of Classification Search
CPC .................. A61B 17/72–17/7291
USPC .............. 606/62–68, 96–98; 623/23.23; 285/140.1, 295, 217, 218; 411/399, 482, 411/501, 504; 403/361
See application file for complete search history.

(56) References Cited

U.S. PATENT DOCUMENTS 2,834,342 A 5/1958 Yost
3,255,747 A 6/1966 Cochran et al.
3,433,220 A 3/1969 Zickel
(Continued)

FOREIGN PATENT DOCUMENTS

CH 668 173 12/1988
CH 674 613 6/1990
(Continued)

OTHER PUBLICATIONS

International Search Report for International Application No. PCT/CH03/00376, mailed Feb. 26, 2004, German language version.
(Continued)

Primary Examiner — Jan Christopher Merene
Assistant Examiner — Steven Cotroneo
(74) Attorney, Agent, or Firm — Fay Kaplun & Marcin, LLP

(57) ABSTRACT

Described herein is a surgical nail in the form of an intramedullary nail with a central axis made from a material M with a tensile strength $F_z$, compressive strength $F_d$, density $\rho_2$ and modulus of elasticity E. The nail has a transverse bore extending transversely to the central axis and having a cross-sectional profile F and a transverse axis, the cross-sectional profile F having a maximum length a that runs in the direction of the central axis and a maximum width b that runs perpendicular to the length. An insert with the longitudinal axis, made from material m and having a modulus of elasticity e that is smaller than the modulus of elasticity E of material M, can be introduced into the transverse bore. The insert also has a length L that runs in the direction of its longitudinal axis and satisfies the condition L>0.2 D.

19 Claims, 3 Drawing Sheets

(56) References Cited

U.S. PATENT DOCUMENTS

| | | | |
|---|---|---|---|
| 4,095,591 A | 6/1978 | Graham, Jr. et al. | |
| 4,103,683 A | 8/1978 | Neufeld | |
| 4,172,452 A | 10/1979 | Forte et al. | |
| 4,274,163 A | 6/1981 | Malcom et al. | |
| 4,438,762 A | 3/1984 | Kyle | |
| 4,494,535 A | 1/1985 | Haig | |
| 4,612,920 A | 9/1986 | Lower | |
| 4,621,628 A | 11/1986 | Brudermann | |
| 4,622,959 A | 11/1986 | Marcus | |
| 4,657,001 A | 4/1987 | Fixel | |
| 4,697,585 A | 10/1987 | Williams | |
| 4,705,027 A | 11/1987 | Klaue | |
| 4,754,749 A | 7/1988 | Tsou | |
| 4,776,330 A | 10/1988 | Chapman et al. | |
| 4,791,918 A | 12/1988 | Von Hasselbach | |
| 4,817,591 A | 4/1989 | Klaue | |
| 4,973,332 A | 11/1990 | Kummer | |
| 4,978,270 A * | 12/1990 | Ackerman | 411/511 |
| 5,032,125 A | 7/1991 | Durham et al. | |
| 5,041,114 A | 8/1991 | Chapman et al. | |
| 5,041,115 A | 8/1991 | Frigg et al. | |
| 5,120,171 A | 6/1992 | Lasner | |
| 5,167,663 A | 12/1992 | Brumfield | |
| 5,176,681 A | 1/1993 | Lawes et al. | |
| 5,300,074 A | 4/1994 | Frigg | |
| 5,312,406 A | 5/1994 | Brumfield | |
| 5,364,398 A | 11/1994 | Chapman et al. | |
| 5,454,813 A * | 10/1995 | Lawes | 606/62 |
| 5,484,439 A | 1/1996 | Olson et al. | |
| 5,531,748 A * | 7/1996 | de la Caffiniere | 606/62 |
| 5,549,610 A | 8/1996 | Russell et al. | |
| 5,573,536 A | 11/1996 | Grosse et al. | |
| 5,578,035 A | 11/1996 | Lin | |
| 5,591,168 A | 1/1997 | Judet et al. | |
| 5,658,287 A | 8/1997 | Hofmann et al. | |
| 5,658,339 A | 8/1997 | Tronzo et al. | |
| 5,713,901 A | 2/1998 | Tock | |
| 5,713,902 A | 2/1998 | Friedl | |
| 5,728,099 A | 3/1998 | Tellman et al. | |
| 5,741,256 A | 4/1998 | Bresina | |
| 5,772,662 A | 6/1998 | Chapman et al. | |
| 5,908,422 A | 6/1999 | Bresina | |
| 5,928,235 A | 7/1999 | Friedl | |
| 5,935,127 A | 8/1999 | Border | |
| 5,976,139 A | 11/1999 | Bramlet | |
| 5,976,141 A * | 11/1999 | Haag et al. | 606/292 |
| 6,010,506 A | 1/2000 | Gosney et al. | |
| 6,059,785 A | 5/2000 | Schavan et al. | |
| 6,123,708 A | 9/2000 | Kilpela et al. | |
| 6,126,661 A | 10/2000 | Faccioli et al. | |
| 6,187,007 B1 | 2/2001 | Frigg et al. | |
| 6,296,645 B1 | 10/2001 | Hover et al. | |
| 6,454,810 B1 | 9/2002 | Lob | |
| 6,645,209 B2 * | 11/2003 | Hall et al. | 606/281 |
| 6,652,528 B2 * | 11/2003 | Vandewalle | 606/62 |
| 6,783,529 B2 * | 8/2004 | Hover et al. | 606/62 |
| 7,182,765 B2 | 2/2007 | Roth et al. | |
| 2002/0151898 A1 | 10/2002 | Sohngen et al. | |
| 2002/0173792 A1 | 11/2002 | Severns et al. | |
| 2003/0069581 A1 | 4/2003 | Stinson et al. | |
| 2003/0114855 A1 | 6/2003 | Wahl et al. | |
| 2006/0064095 A1 | 3/2006 | Senn et al. | |
| 2006/0111716 A1 | 5/2006 | Schlienger et al. | |
| 2006/0161155 A1 | 7/2006 | Schlienger et al. | |
| 2006/0189988 A1 | 8/2006 | Schlienger et al. | |
| 2006/0235395 A1 | 10/2006 | Frigg et al. | |
| 2006/0241605 A1 | 10/2006 | Schlienger et al. | |

FOREIGN PATENT DOCUMENTS

| | | |
|---|---|---|
| DE | 196 29 011 A1 | 1/1998 |
| DE | 199 45 611 A1 | 9/2001 |
| EP | 0 251 583 A2 | 1/1988 |
| EP | 0 321 170 B1 | 6/1989 |
| EP | 0 381 462 A2 | 8/1990 |
| EP | 0 411 273 A1 | 2/1991 |
| EP | 0 471 418 A1 | 2/1992 |
| EP | 0 838 199 A1 | 4/1998 |
| EP | 0 845 245 A2 | 6/1998 |
| EP | 0 853 923 A1 | 7/1998 |
| EP | 0 919 200 A1 | 6/1999 |
| EP | 0 968 685 A2 | 6/1999 |
| EP | 1 053 718 A1 | 11/2000 |
| EP | 1 214 914 A2 | 6/2002 |
| EP | 1 260 188 A1 | 11/2002 |
| FR | 2 784 283 | 4/2000 |
| GB | 2209947 A | 6/1989 |
| JP | 09-066059 | 3/1997 |
| JP | 09-066060 | 3/1997 |
| JP | 09-066061 | 3/1997 |
| JP | 11-137566 | 5/1999 |
| JP | 2000-051224 | 2/2000 |
| JP | 2000-051225 | 2/2000 |
| JP | 2000-342596 | 12/2000 |
| WO | WO 93/15679 | 8/1993 |
| WO | WO 96/15737 | 5/1996 |
| WO | WO 97/37606 | 10/1997 |
| WO | WO 98/05263 | 2/1998 |
| WO | WO 98/30164 | 7/1998 |
| WO | WO 98/41161 | 9/1998 |
| WO | WO 98/46169 | 10/1998 |
| WO | WO 00/67653 | 11/2000 |
| WO | WO 02/060331 | 8/2002 |
| WO | WO 03/015649 | 2/2003 |

OTHER PUBLICATIONS

International Search Report for International Application No. PCT/CH03/00376, mailed Feb. 26, 2004, English language translation of the German language version.

International Preliminary Examination Report for International Application No. PCT/CH03/00376, completed Sep. 21, 2005, German language version.

International Preliminary Examination Report for International Application No. PCT/CH03/00376, completed Sep. 21, 2005, English language translation of the German language version.

* cited by examiner

SURGICAL NAIL

RELATED APPLICATION DATA

The present application is a continuation of the U.S. National Stage designation of co-pending International Patent Application No. PCT/CH2003/000376, filed Jun. 12, 2003, the entire content of which is expressly incorporated herein by reference thereto.

FIELD OF THE INVENTION

The invention relates to a surgical nail and, more particularly, to an intramedullary nail having a longitudinal axis and an insert for insertion into a transverse bore through the intramedullary nail.

BACKGROUND OF THE INVENTION

The locking of intramedullary nails is known in the art. The introduction of locking screws or locking bolts (hereinafter referred to collectively as "locking screws") into the transverse bores of a intramedullary nail is carried out either with the aid of an imaging process (X-ray control) or a relatively complicated aiming device. In both cases, a certain aiming inaccuracy is unavoidable because the tip of the screw cannot be aligned exactly coaxially with the central axis of the transverse bore, and instead deviates therefrom by a certain amount. In order to enable the locking screw to enter into and pass through the transverse bore despite this aiming error, the outside diameter of the screw is underdimensioned such that it will be less than the diameter of the transverse bore. If the aiming accuracy remains within the range of this underdimensioning, the locking screw can be guided, despite the aiming error, through the transverse bore without any problem. In any case, as a result of the underdimensioning, the locking screw has a certain play or clearance relative to the transverse bore.

This clearance defines the amount by which the main bone fragments, which are fixed by means of locking screws in the corresponding locking hole, can move relative to the nail, and, because of the rigidity of the nail, move relative to the other main bone fragments fastened with the same nail. While some play or clearance is essential to guarantee the usefulness of the locking for surgeons, in the case of some indications (e.g. in the case of metaphysial fragments) it is clinically undesirable.

Even nails with a solid cross-section, that may have an internal thread in the locking hole, are not without clearance. The internal thread merely prevents the axial displacement of the nail on the locking screw.

U.S. Pat. No. 6,296,645 to Hover et al. discloses a hollow, metallic intramedullary nail with diametrally opposed openings on the jacket of the transverse bore, described as windows, having one or two plastic inserts through which the locking screw can be introduced. A disadvantage of this known intramedullary nail is that the window-like plastic inserts can be easily pushed in, such that their desired function is lost. Even with a careful manipulation, the two plastic inserts can be pushed out from their "windows," which also leads to a loss of function.

SUMMARY OF THE INVENTION

The present invention seeks to remedy this problem. The object of the invention is to produce a surgical nail, in particular an intramedullary nail, where the clearance between the nail and the locking screw can be eliminated without any risk, and where an improved holding force and improved guiding can be achieved between the locking screw and the intramedullary nail.

The invention achieves the objective stated with a surgical nail having an elongate body with a longitudinal central axis and at least one transverse bore extending transversely to the central axis, the transverse bore having a cross-section F and a transverse axis. An insert is configured and dimensioned for insertion into the transverse bore, the insert having a longitudinal axis and a plurality of projections provided on an outer surface of the insert for engaging the nail body adjacent to the transverse and holding the insert in position within the transverse bore.

The following advantages can be achieved with the present invention:

a) the aiming accuracy during the insertion of the locking screw is unimpaired;

b) the doctor is in the position to decide during the operation whether he uses an angularly stable locking of the locking screw or not, while the term "angularly stable" stands for a certain limitation of the degree of freedom;

c) the feasibility of an angularly stable fixing of the bone fragments in certain directions for a certain amount of the load; and d) the nail and the insert can be packed separately in a sterile manner and the surgeon can choose whether he uses the nail without or with the insert. In the latter case the surgeon himself can insert the insert into the nail and, if necessary, remove it. If the surgeon uses the nail without an insert, it remains in the sterile package for the next occasion.

In the case of one particular embodiment, the length L of the insert satisfies the condition L>0.5 D and preferably L=D. In the case of a further embodiment the insert is basically congruent with the transverse bore.

In the case of a particular embodiment, the insert can have a bore that is coaxial with its longitudinal axis in order to facilitate the introduction of the locking screw. The material m of the insert may have a tensile strength $f_z<F_z$, a compressive strength $f_d<F_d$ and modulus of elasticity e<0.8 E, preferably e<0.7 E, where $F_z$, $F_d$ and E are the tensile strength, compressive strength and modulus of elasticity, respectively, of the intramedullary nail.

In another embodiment, the material m of the insert is a biocompatible material, preferably a polyethylene or a high-molecular polyethylene (HMVVPE), which advantageously, as a synthetic material, will not disintegrate into unknown decomposing products.

According to another preferred embodiment, the insert is made from a material of lesser hardness, such as a bioabsorbable polymer, preferably a polylactide. The result of this execution is an initial clearance-free transverse locking of the intramedullary nail, which, with the gradual absorption of the polymer, is successively discontinued, so that the transverse locking screws will eventually become mobile relative to the intramedullary nail and the bone fragments involved. Thus, following the consolidation of the fracture, a dynamization of the bone fragments takes place. The bioabsorbable material also has the advantage that the splinters caused by screwing in the locking screw into the nail can be decomposed by the body. A further advantage is the possibility to realize, as time passes, a different strength of the angularly stable locking of the locking screw, i.e. to achieve a gradual reduction of the holding force.

The transverse bore of the intramedullary nail can be either a circular bore, whereby the cross-section F has the maximum lengths a=b (i.e. a=b is the diameter of the transverse bore), or a slotted hole, whereby the cross-section F has the maximum lengths a>b.

The material m of the insert has preferably a lower density $\rho_1$ than the material M with density $\rho_2$, and preferably $\rho_1 < 0.8\,\rho_2$.

The locking screws or locking bolts, which can be passed through the insert, should preferably have a shaft with a diameter of d (maximum diameter that includes a possible external thread), that satisfies the condition a>d<b. At the same time the diameter d of the external thread should preferably be at least 5% smaller than the smaller of the two dimensions a, b.

In the case of a special execution, the transverse bore expands towards the surface of the nail, preferably in the form of a tapered section. The advantage of this is that an insert having a corresponding tapered section that is inserted into it cannot be axially displaced in the direction of insertion.

BRIEF DESCRIPTION OF THE DRAWINGS

The invention and further developments of the invention are explained in detail based on the partially schematic illustrations of several embodiments, in which.

DETAILED DESCRIPTION OF THE PREFERRED EMBODIMENTS

Figure 1:
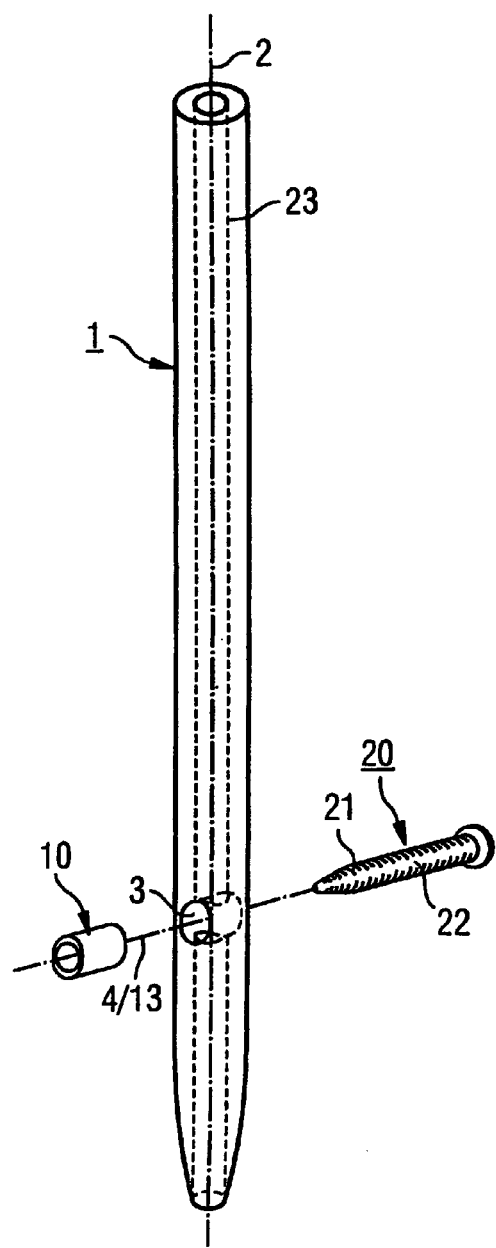
FIG. 1 shows a perspective view of a intramedullary nail having a continuous cannula with a transverse bore to be fitted with an insert and a transverse locking screw.
Figure 2:
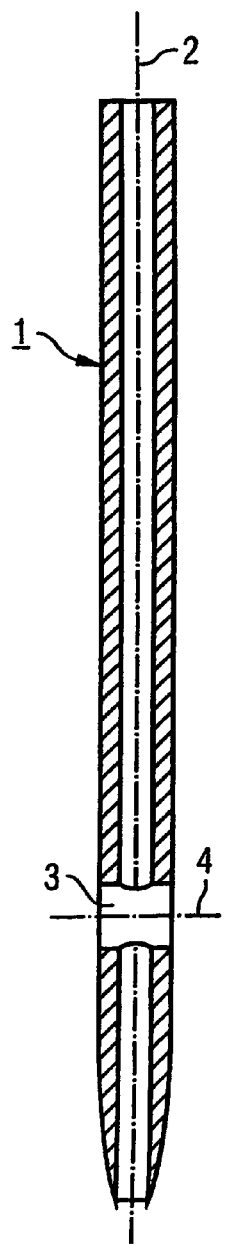
FIG. 2 shows a longitudinal section through the intramedullary nail according to FIG. 1.
Figure 3:
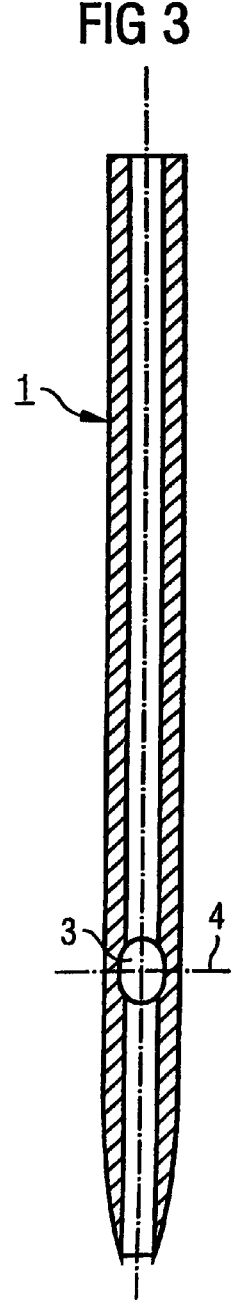
FIG. 3 shows a longitudinal section through the intramedullary nail according to FIG. 1, rotated by 90°.
Figure 4:
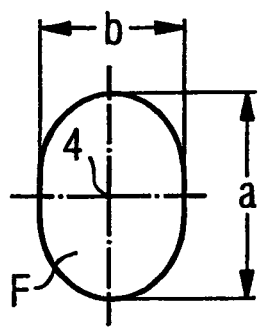
FIG. 4 shows an enlarged schematic view of the section of the transverse bore of the intramedullary nail according to FIG. 1.

The surgical nail 1 illustrated in FIGS. 1-3 is an intramedullary nail for hollow bones with a central axis 2, that is made from a metal or a metal alloy, i.e. a material with relatively high strength (tensile strength $F_z$, compression strength $F_d$ and modulus of elasticity E). The nail 1 has a transverse bore 3, having a transverse axis 4 and extending as a slotted hole with the cross-section F towards the central axis 2. As illustrated in FIG. 4, the transverse bore 3 has a cross-section F, that has its maximum length a in the direction of the central axis 2 and its maximum width b perpendicular to the length a. The nail can have further transverse bores (circular or oval), which are not illustrated.

As illustrated in FIG. 1, an insert 10 is provided to be introduced into the transverse bore 3. The dimensions of the insert 10 are congruent with that of the transverse bore 3 or are so chosen that its insertion results in a press fit, thus preventing the insert from falling out of the transverse bore 3. The insert 10 is made from a material m with lesser strength and, in particular, with a lower modulus of elasticity (when compared with the material M of the intramedullary nail).

Figure 5:
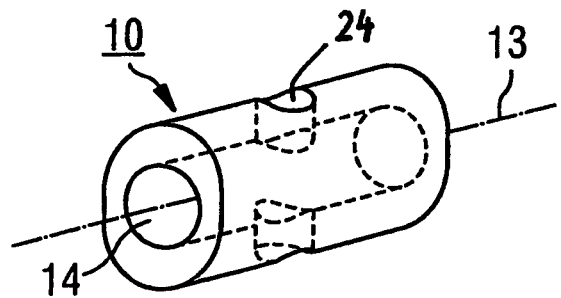
FIG. 5 shows a single-piece insert with a longitudinal bore aligned with the central axis of the transverse bore in the intramedullary nail, and a transverse bore that, after insertion, is approximately aligned with the cannula of the intramedullary nail.

As illustrated in FIG. 5, the insert 10 can have a longitudinal bore 14 that is coaxial with its longitudinal axis 13 and a transverse bore 24 that, after its insertion into the intramedullary nail in the proper orientation, is aligned with the cannula of the intramedullary nail.

Figure 6:
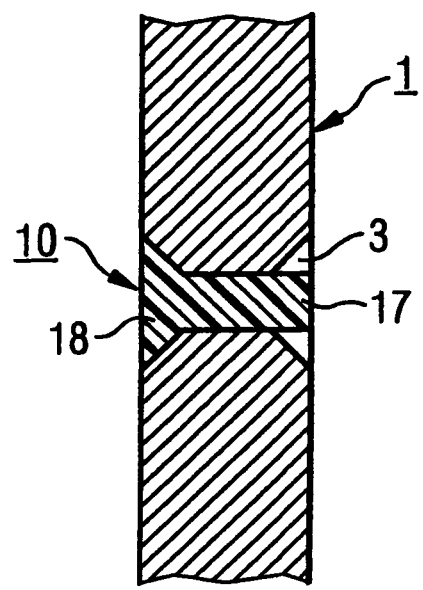
FIG. 6 shows a partial longitudinal section through a further, modified intramedullary nail with a modified single-piece insert.

In FIG. 6 a version of the single-piece insert 10 is illustrated that comprises a pin 17 with a tapered expanding head 18.

Figure 7:
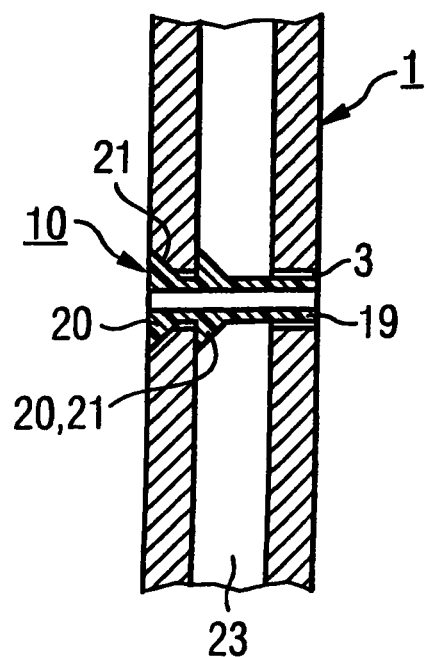
FIG. 7 shows a partial longitudinal section through a further, modified intramedullary nail with a modified single-piece insert.

In FIG. 7 a further version of a single-piece insert 10 is illustrated, that comprises a pin 19 with a bore centrally passing through it as well as a plurality of tapered expansions 20 provided on the circumference, that, in the form of a click lock, can engage corresponding cavities 21 or the longitudinal bore 23 in the region of the transverse bore 3.

What is claimed is:

1. An intramedullary nail comprising:
    an elongate body having a longitudinal central axis and formed of a material M having a tensile strength $F_z$, compressive strength $F_d$, density $\rho_2$ and modulus of elasticity E;
    at least one transverse bore extending transversely to the central axis from a first end to a second end, the transverse bore having a cross-section F and a transverse axis, the transverse bore including a first tapered region tapering from a first diameter at the first end to a second reduced diameter toward a center region of the transverse bore; and
    an insert formed of a bioabsorbable material configured and dimensioned for removable insertion into the transverse bore, wherein the transverse bore is manufactured with a size and shape selected to permit insertion of the insert thereinto such that a central bore of the insert is coaxial with the transverse axis, the insert extending from a first end to a second end along a longitudinal axis and including a tapered portion at the first end conforming to dimensions of the tapered region of the transverse bore to hold the insert in position within the transverse bore, the insert including a central bore coaxial with the transverse axis.

2. The device of claim 1, wherein the insert is formed of a material m having a modulus of elasticity e<E.

3. The device of claim 2, wherein the modulus of elasticity of the insert, e<0.8 E.

4. The device of claim 2, wherein the material m has a tensile strength $f_z < F_z$.

5. The device of claim 2, wherein the material m has a compressive strength $f_d < F_d$.

6. The device of claim 2, wherein the density $\rho_1$ of material m is less than the density $\rho_2$ of material M.

7. The device of claim 1, wherein the transverse cross-section F of the transverse bore has a maximum length a in the direction of the central axis and a maximum width b perpendicular to the length a, the intramedullary nail has a diameter D at the transverse bore, and the insert has a length L in the direction of its longitudinal axis that satisfies the condition L>0.2 D.

8. The device of claim 7, wherein the insert has a length L>0.5 D.

9. The device of claim 7, wherein the transverse bore in the nail has a substantially circular cross-section F, with maximum lengths a=b.

10. The device of claim 7, wherein the transverse bore in the nail has a substantially slotted cross-section F, where the maximum length a>b.

11. The device of claim 1, wherein the insert has substantially the same shape as the transverse bore.

12. The device of claim 1, wherein the bioabsorbable material includes one of a polyethylene, a high-molecular polyethylene (HMWPE), and another biocompatible synthetic material.

13. The device of claim 1, wherein the bioabsorbable material is one of a polymer and a copolymer.

14. The device of claim 1, further comprising a locking screw adapted for insertion through the insert in the transverse bore, the locking screw having a shaft with an outer diameter d satisfying the conditions a>d<b.

15. The device of claim 1, wherein the nail has an outer surface adjacent the transverse bore, and the transverse bore expands towards the first end adjacent to the outer surface of the nail to form a depression in the outer surface of the nail.

16. The device of claim 1, wherein the insert is a pin.

17. The device of claim 1, wherein the transverse bore further comprises a second tapered region tapering from the first diameter at the second end of the transverse bore to the second reduced diameter toward the center region of the transverse bore.

18. An intramedullary nail comprising:
an elongate body having a longitudinal central axis and an outer surface;
at least one transverse bore extending transversely to the central axis from a first end to a second end, the transverse bore having a cross-section F and having a tapered region expanding from a first diameter at a center region thereof towards a second diameter toward the first end adjacent to the outer surface of the nail to form at least one depression in the outer surface of the nail; and
an insert formed of a bioabsorbable material configured and dimensioned for removable insertion into the transverse bore, the insert having a longitudinal axis, a central bore formed along the longitudinal axis and coaxial with the transverse bore, the insert extending from a first end to a second end and including a tapered portion at the first end conforming to dimensions of the tapered region of the transverse bore to hold the insert in position within the transverse bore, wherein the transverse bore is manufactured with a size and shape selected to permit insertion of the insert thereinto;
wherein the insert is formed of a material m having a modulus of elasticity e less than the modulus of elasticity E of the nail.

19. A method for repairing bone fractures comprising:
introducing an intramedullary nail within the medullary canal of a bone, the intramedullary nail having an elongate body with a longitudinal central axis and at least one transverse bore extending transversely to the central axis, the transverse bore having a cross-section F and a transverse axis;
inserting an insert formed of a bioabsorbable material into the transverse bore of the nail, the insert having a longitudinal axis, a central bore formed along the longitudinal axis and coaxial with the transverse axis, and a projection provided on an outer surface of the insert for engaging the nail body adjacent to the transverse bore and holding the insert in position within the transverse bore, wherein the transverse bore is manufactured with a size and shape selected to permit insertion of the insert thereinto; and
introducing a fixation element through the central bore of the insert and the transverse bore of the nail to lock the nail in position,
wherein the insert is formed of a material m having a modulus of elasticity e less than the modulus of elasticity E of the nail.

* * * * *